USO05811285A

United States Patent [19]
Gray et al.

[11] Patent Number: 5,811,285
[45] Date of Patent: Sep. 22, 1998

[54] DSZD UTILIZATION IN DESULFURIZATION OF DBT BY RHODOCOCCUS SP. IGTS8

[75] Inventors: Kevin A. Gray; Charles H. Squires; Daniel J. Monticello, all of The Woodlands, Tex.

[73] Assignee: Energy BioSystems Corporation, The Woodlands, Tex.

[21] Appl. No.: 715,554

[22] Filed: Sep. 19, 1996

[51] Int. Cl.$^6$ .............................. C12N 1/20; C12N 15/00; C07H 21/04

[52] U.S. Cl. .................................... 435/252.3; 435/252.3; 435/320.1; 536/23.3; 935/22

[58] Field of Search .......................... 536/23.2; 435/282, 435/320.1, 325, 252.3

[56] References Cited

U.S. PATENT DOCUMENTS

| 5,002,888 | 3/1991 | Kilbane, II | 435/252.31 |
|---|---|---|---|
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |
| 5,344,778 | 9/1994 | Kilbane, II | 435/262 |
| 5,356,801 | 10/1994 | Rambosek et al. | 435/195 |
| 5,356,813 | 10/1994 | Monticello | 435/282 |
| 5,358,870 | 10/1994 | Monticello et al. | 435/282 |

FOREIGN PATENT DOCUMENTS

94/01563  1/1994  WIPO .

OTHER PUBLICATIONS

Monticello, Daniel, J. and Kilbane, John J., "Practical Considerations in Biodesulfurization of Petroleum," IGT's Third International Symposium on Gas, Oil, Coal and Environmental Biotechnology (Dec. 3–5 1990), New Orleans, LA.

Denome, Sylvia A. et al., "Characterization of the Desulfurization Genes from Rhodococcus sp. Strain IGTS8,"*Journal of Bacteriology* 176(21):6707–6716 (1994).

Lei, Benfang et al., "*Vibrio harveyi* NADPH–Flavin Oxidoreductase: Cloning, Sequencing and Overexpression of the Gene and Purification and Characterization of the Cloned Enzyme," *Journal of Bacteriology* 176(12):3553–3558 (1994).

Ohshiro, Takashi et al., "Enzymatic desulfurization of dibenzothiopene by a cell–free system of *Rhodococcus erythropolis* D–1," *FEMS Microbiology Letters*, 118:341–344 (1994).

Ohshiro, Takashi et al., "Involvement of Flavin Coenzyme in Dibenzothiophene Degrading Enzyme System from *Rhodococcus erythropolis* D–1," *Biosci, Biotech. Biochem.*, 59(7):1349–1351 (1995).

Piddington, Christopher S. et al., "Sequence and Molecular Characterization of a DNA Region Encoding the Dibenzothiophene Desulfurization Operon of Rhodococcus sp. Strain IGTS8,"*Applied and Environmental Microbiology*, 61(2):468–475 (1995).

Nagy, István et al., "Characterization of the Rhodococcus sp. NI86/21 gene encoding alcohol: N,N'–dimethyl–4–nitrosoaniline oxidoreductase inducible by atrazine and thiocarbamate herbicides," *Arch Microbiol.*, 163:439–446 (1995).

Parry, Ronald J. et al., "Cloning, Analysis, and Overexpression of the Gene Encoding Isobutylamine N–Hydroxylase from the Valanimycin Producer, *Streptomyces viridifaciens*," *Journal of Bacteriology*, 179(2):409–416 (1997).

Arunachalam, Usha et al., "Mechanism of p–Hydroxyphenylacetate–3–hydroxylase," *The Journal of Biological Chemistry*, 269(1):150–155 (1994).

Lei, Benfang and Tu, Shiao–Chun, "Gene Overexpression, Purification, and Identification of a Desulfurization Enzyme from Rhodococcus sp. Strain IGTS8 as a Sulfide/Sulfoxide Monooxygenase," *Journal of Bacteriology*, 178(19):5699–5705 (1996).

Arunachalam, Usha et al., "p–Hydroxyphenylacetate–3–hydroxylase," *The Journal of Biological Chemistry*, 267(36):25848–25855 (1992).

Kendrew, Steven G. et al., "Identification of a Flavin:NADH Oxidoreductase Involved in the Biosynthesis of Actinorhodin," *The Journal of Biological Chemistry*, 270(29):17339–17343 (1995).

Thibaut, Dennis et al., "Purification of the Two–Enzyme System Catalyzing the Oxidation of the D–Proline Residue of Pristinamycin II$_B$ during the Last Step of Pristinamycin II$_A$ Biosynthesis," *Journal of Bacteriology*, 177(18):5199–5205 (1995).

(List continued on next page.)

*Primary Examiner*—Rebecca E. Prouty
*Assistant Examiner*—Einar Stole
*Attorney, Agent, or Firm*—Hamilton, Brooks, Smith & Reynolds, P.C.

[57] ABSTRACT

The invention relates to the discovery that the rate of reaction of the desulfurization of fossil fuels is enhanced by the addition of an oxidoreductase to the biocatalyst. The invention is drawn to a method for enhancing the rate of desulfurizing a fossil fuel containing organic sulfur compounds, comprising the steps of:

a) contacting the fossil fuel with an aqueous phase containing a biocatalyst capable of cleaving carbon-sulfur bonds and a rate-enhancing amount of an oxidoreductase, thereby forming a fossil fuel and aqueous phase mixture;

b) maintaining the mixture of step (a) under conditions sufficient for cleavage of the carbon-sulfur bonds of the organic sulfur molecules by the biocatalyst, thereby resulting in a fossil fuel having a reduced organic sulfur content; and c) separating the fossil fuel having a reduced organic sulfur content from the resulting aqueous phase. The invention also relates to a recombinant microorganism containing one or more recombinant DNA molecules which encode a biocatalyst capable of desulfurizing a fossil fuel containing organic sulfur molecules and which encode an oxidoreductase. The invention also relates to a composition comprising (a) a biocatalyst capable of desulfurizing a fossil fuel containing organic sulfur molecules and (b) an oxidoreductase.

15 Claims, 6 Drawing Sheets

OTHER PUBLICATIONS

Blanc, Véronique et al., "Cloning and Analysis of Structural Genes from *Streptomyces pristinaespiralis* Encoding Enzymes Involved in the Conversion of Pristinamycin $II_B$ to Pristinamycin $II_A$ ($PII_A$): $PII_A$ Synthase and NADH:Riboflavin 5'–Phosphate Oxidoreductase," *Journal of Bacteriology*, 177(18):5206–5214 (1995).

Knobel, Hans–Rudolf et al., "Cloning and Characterization of the Genes Encoding Nitrilotriacetate Monooxygenase of *Chelatobacter heintzii* ATCC 29600," *Journal of Bacteriology*, 178(21):6123–6132 (1996).

Uetz, Thomas et al., "Purification and Characterization of a Two–Component Monooxygenase That Hydroxylates Nitrilotriacetate from Chelatobacter Strain ATCC 29600," *Journal of Bacteriology*, 174(4):1179–118 (1992).

Fernández–Moreno, Miguel A. et al., "Nucleotide Sequence and Deduced Functions of a Set of Cotranscribed Genes of *Streptomyces coelicolor* A3 (2) Including the Polyketide Synthase for the Antibiotic Actinorhodin," *The Journal of Biological Chemistry*, 267(27):19278–19290 (1992).

Prieto, María A. and Garcia, Jos´´L., "Molecular Characterization of 4–Hydroxyphenylacetate 3–Hydroxylase of *Escherichia coli*," *The Journal of Biological Chemistry*, 269 (36) :22823–22829 (1994).

Gray, Kevin A. et al., "Molecular mechanisms of biocatalytic desulfurization of fossil fuels," *Nature Biotechnology*, 14:1705–1709 (1996).

Xi, L et al., "A Flavin Reductase Stimulates DszA and DszC Proteins of *Rhodococcus erythropolis* IGTS8 in Vitro" *Biochemical and Biophysical Research Communications*, 230:73–75 (1997).

```
GGTACCTCGACTGTCGTCATCGCGAAGCTAGTCCTCTCGTGAAGCTGGGTAAAGCGCAGGTCAGTGAAGTGC      72
AACATCTAGAACGTGTTCTAGTTCAATGTTAGCAGTGATGAAAAGCTACTGGGGATCGTAGTCGCCGAGCAA     144
CACGTTCCCGATCAGCGGGAACCACGGCAGTCTGATCCGGCCTTCCTGGCGGTCCGGGGTGGCGACGACCTG     216
CCCGAACGGGCGGTTCGCCGGCGGCGTCCGGGCGGTTGAGCTGCCGAAGTCTGTGCACGGGGTGTTTGTCGG     288
TACACAGTGGGAACCAGGTGAGACGCCGGTCACAAAGAATCGGCTCGAATCCCTCCCGCAGTCATATTCGTG     360
CACATCCATGAGGAGATACCGATGGCTATCGAGCTCAACCAGATCTGGGACTTTCCGATCAAGGAGTTCCAC     432
                 M   A   I   E   L   N   Q   I   W   D   F   P   I   K   E   F   H
CCCTTCCCGCGCGCCCTGATGGGTGTGGGCGCTCACGACATCATCGGTGTGGAGGCCAAGAATCTCGGCTTC     504
  P   F   P   R   A   L   M   G   V   G   A   H   D   I   I   G   V   E   A   K   N   L   G   F
AAGCGCACCCTTCTGATGACGACCGGTCTGCGCGGTTCGGGCATCATCGAGGAACTCGTCGGCAAGATCGAG     576
  K   R   T   L   L   M   T   T   G   L   R   G   S   G   I   I   E   E   L   V   G   K   I   E
TACCAGGGTGTCGAGGTCGTGCTCTACGACAAGGTCGAGTCGAATCCCAAGGACTACAACGTCATGGAGGCC     648
  Y   Q   G   V   E   V   V   L   Y   D   K   V   E   S   N   P   K   D   Y   N   V   M   E   A
GCGGCTCTCTATCAGAAGGAGAAGTGCGACTCGATCATCTCGATCGGCGGTGGTTCGAGCCACGACGCCGCC     720
  A   A   L   Y   Q   K   E   K   C   D   S   I   I   S   I   G   G   G   S   S   H   D   A   A
AAGGGTGCTCGCGTCGTGATCGCACACGACGGTCGCAACATCAACGAGTTCGAGGGCTTCGCCAAGTCCACC     792
  K   G   A   R   V   V   I   A   H   D   G   R   N   I   N   E   F   E   G   F   A   K   S   T
AACAAGGAGAACCCGCCGCATATCGCCGTATCCACTACGGCTGGAACGGGTTCCGAGACGTCGTGGGCATAC     864
  N   K   E   N   P   P   H   I   A   V   S   T   T   A   G   T   G   S   E   T   S   W   A   Y
GTCATCACTGACACCTCGGACATGAACAACCCGCACAAGTGGGTGGGCTTCGACGAGGCGACCATCGTCACG     936
  V   I   T   D   T   S   D   M   N   N   P   H   K   W   V   G   F   D   E   A   T   I   V   T
TTGGCGATCGACGATCCGCTGCTCTACTACACCTGCCCTCAGCATTTCACCGCGTACTGCGGCTTCGACGTA    1008
  L   A   I   D   D   P   L   L   Y   Y   T   C   P   Q   H   F   T   A   Y   C   G   F   D   V
CTCGCGCACGGCAGTGAGCCTTTCGTTTCTCGTCTCGATTTCGCGCCTTCGCTCGGTAACGCGATCTACTCG    1080
  L   A   H   G   S   E   P   F   V   S   R   L   D   F   A   P   S   L   G   N   A   I   Y   S
GTCGAGTTGGTCGCGAAGAACCTGCGCGAGGCCGTCTTCGAGCCGCGTAACCTCAAGGCGCGCGAGGGAATG    1152
  V   E   L   V   A   K   N   L   R   E   A   V   F   E   P   R   N   L   K   A   R   E   G   M
ATGAACGCGCAGTACATTGCCGGACAGGCCTTCAACTCCGGTGGCCTCGGCATCGTTCACTCGATCTCGCAC    1224
  M   N   A   Q   Y   I   A   G   Q   A   F   N   S   G   G   L   G   I   V   H   S   I   S   H
GCGGTCAGTGCATTCTTCGACAGCCACCACGGTTTGAACAACGCCATCGCGTTGCCGCGTGTGTGGGAGTAC    1296
  A   V   S   A   F   F   D   S   H   H   G   L   N   N   A   I   A   L   P   R   V   W   E   Y
AACCTGCCTTCGCGTTACGAGCGCTACGCCCAGTTGGCCGGCGCACTCGGTGTCGACACTCGCAACCTCACC    1368
  N   L   P   S   R   Y   E   R   Y   A   Q   L   A   G   A   L   G   V   D   T   R   N   L   T
ACGGTTCAGGCCGCGGATGCTGCCGTCGAGGCTGCCATTCGTCTGGCCAAGGACGTCGGTATCCCCGACAAC    1440
  T   V   Q   A   A   D   A   A   V   E   A   A   I   R   L   A   K   D   V   G   I   P   D   N
TTCGGGCAGGTTCGCACAGACTCGTACGCGAAGAACCAGATGAACACCAAGAAGTACGAGGGTCGTGGTGAT    1512
  F   G   Q   V   R   T   D   S   Y   A   K   N   Q   M   N   T   K   K   Y   E   G   R   G   D
GTCATCAAGGGTGACGAGAAGACTGTGCGCGCCATCTCCGAGCACATTCAGGACGACTGGTGCACCCCGGGT    1584
  V   I   K   G   D   E   K   T   V   R   A   I   S   E   H   I   Q   D   D   W   C   T   P   G
AACCCCCGTGAGGTCACTGTGGAGTCGATGATCCCGGTTGTCGATCACGCGATCAACAAGTCGTACTTCTAG    1656
  N   P   R   E   V   T   V   E   S   M   I   P   V   V   D   H   A   I   N   K   S   Y   F
CAGGGCCTCCGGCCCCGTGCGCGCTTAAGGAGTCCAGAGACTCCTCGAGCGCGCACAGGGGCTGTGCCCCTA    1728
TCGAAAGGTATTCCATGTCCGGTCGCAGTTTCTCCAGCGGAATCGAAGTGAAAGATGCTCTGCGAGAGCAGG    1800
                 M   S   G   R   S   F   S   S   G   I   E   V   K   D   A   L   R   E   Q
ACTACATTGCCGATGACGAGTTCGCGGTAGTCGTTCATCTGGCGACGGCGCTGGGGCGTCCGCTCCTGCTCG    1872
  D   Y   I   A   D   D   E   F   A   V   V   V   H   L   A   T   A   L   G   R   P   L   L   L
AAGGGCCGGCCGGTGTCGGTAAGACGGAACTGGCGAAGTCTCTGGCTGCGATCGGGGGCCGCAAACTGGTGC    1944
  E   G   P   A   G   V   G   K   T   E   L   A   K   S   L   A   A   I   G   G   R   K   L   V
GATTGCAGTGTTACGAAGGGCTGGACGACAATCGAGCCCTGTACGAATGGGACTACGCGAACGAACTCCTGC    2016
  R   L   Q   C   Y   E   G   L   D   D   N   R   A   L   Y   E   W   D   Y   A   N   E   L   L
ACGTGCAGATGCTTCGCGACCGGATCAGTGATCAGGTTTCCGAATTC                            2063
  H   V   Q   M   L   R   D   R   I   S   D   Q   V   S   E   F
```

Figure 6

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2063 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 382..1652

( i x ) FEATURE:

5,811,285

-continued ( A ) NAME/KEY: CDS
( B ) LOCATION: 1743..2062

( x i ) SEQUENCE DESCRIPTION: SEQ ID NO:1:

```
GGTACCTCGA CTGTCGTCAT CGCGAAGCTA GTCCTCTCGT GAAGCTGGGT AAAGCGCAGG      60

TCAGTGAAGT GCAACATCTA GAACGTGTTC TAGTTCAATG TTAGCAGTGA TGAAAAGCTA     120

CTGGGGATCG TAGTCGCCGA GCAACACGTT CCCGATCAGC GGGAACCACG GCAGTCTGAT     180

CCGGCCTTCC TGGCGGTCCG GGGTGGCGAC GACCTGCCCG AACGGGCGGT TCGCCGGCGG     240

CGTCCGGGCG GTTGAGCTGC CGAAGTCTGT GCACGGGGTG TTTGTCGGTA CACAGTGGGA     300

ACCAGGTGAG ACGCCGGTCA CAAAGAATCG GCTCGAATCC CTCCCGCAGT CATATTCGTG     360

CACATCCATG AGGAGATACC G ATG GCT ATC GAG CTC AAC CAG ATC TGG GAC       411
                        Met Ala Ile Glu Leu Asn Gln Ile Trp Asp
                         1               5                       10
```

| | | | | | | | | | | |
|---|---|---|---|---|---|---|---|---|---|---|
| TTT CCG ATC AAG GAG TTC CAC CCC TTC CCG CGC GCC CTG ATG GGT GTG | | | | | | | | | | 459 |
| Phe Pro Ile Lys Glu Phe His Pro Phe Pro Arg Ala Leu Met Gly Val | | | | | | | | | | |
|         15                  20                  25 | | | | | | | | | | |
| GGC GCT CAC GAC ATC ATC GGT GTG GAG GCC AAG AAT CTC GGC TTC AAG | | | | | | | | | | 507 |
| Gly Ala His Asp Ile Ile Gly Val Glu Ala Lys Asn Leu Gly Phe Lys | | | | | | | | | | |
|     30              35              40 | | | | | | | | | | |
| CGC ACC CTT CTG ATG ACG ACC GGT CTG CGC GGT TCG GGC ATC ATC GAG | | | | | | | | | | 555 |
| Arg Thr Leu Leu Met Thr Thr Gly Leu Arg Gly Ser Gly Ile Ile Glu | | | | | | | | | | |
|     45              50              55 | | | | | | | | | | |
| GAA CTC GTC GGC AAG ATC GAG TAC CAG GGT GTC GAG GTC GTG CTC TAC | | | | | | | | | | 603 |
| Glu Leu Val Gly Lys Ile Glu Tyr Gln Gly Val Glu Val Val Leu Tyr | | | | | | | | | | |
| 60              65              70 | | | | | | | | | | |
| GAC AAG GTC GAG TCG AAT CCC AAG GAC TAC AAC GTC ATG GAG GCC GCG | | | | | | | | | | 651 |
| Asp Lys Val Glu Ser Asn Pro Lys Asp Tyr Asn Val Met Glu Ala Ala | | | | | | | | | | |
| 75              80              85              90 | | | | | | | | | | |
| GCT CTC TAT CAG AAG GAG AAG TGC GAC TCG ATC ATC TCG ATC GGC GGT | | | | | | | | | | 699 |
| Ala Leu Tyr Gln Lys Glu Lys Cys Asp Ser Ile Ile Ser Ile Gly Gly | | | | | | | | | | |
|         95              100             105 | | | | | | | | | | |
| GGT TCG AGC CAC GAC GCC GCC AAG GGT GCT CGC GTC GTG ATC GCA CAC | | | | | | | | | | 747 |
| Gly Ser Ser His Asp Ala Ala Lys Gly Ala Arg Val Val Ile Ala His | | | | | | | | | | |
|             110             115             120 | | | | | | | | | | |
| GAC GGT CGC AAC ATC AAC GAG TTC GAG GGC TTC GCC AAG TCC ACC AAC | | | | | | | | | | 795 |
| Asp Gly Arg Asn Ile Asn Glu Phe Glu Gly Phe Ala Lys Ser Thr Asn | | | | | | | | | | |
|         125             130             135 | | | | | | | | | | |
| AAG GAG AAC CCG CCG CAT ATC GCC GTA TCC ACT ACG GCT GGA ACG GGT | | | | | | | | | | 843 |
| Lys Glu Asn Pro Pro His Ile Ala Val Ser Thr Thr Ala Gly Thr Gly | | | | | | | | | | |
| 140             145             150 | | | | | | | | | | |
| TCC GAG ACG TCG TGG GCA TAC GTC ATC ACT GAC ACC TCG GAC ATG AAC | | | | | | | | | | 891 |
| Ser Glu Thr Ser Trp Ala Tyr Val Ile Thr Asp Thr Ser Asp Met Asn | | | | | | | | | | |
| 155             160             165             170 | | | | | | | | | | |
| AAC CCG CAC AAG TGG GTG GGC TTC GAC GAG GCG ACC ATC GTC ACG TTG | | | | | | | | | | 939 |
| Asn Pro His Lys Trp Val Gly Phe Asp Glu Ala Thr Ile Val Thr Leu | | | | | | | | | | |
|         175             180             185 | | | | | | | | | | |
| GCG ATC GAC GAT CCG CTG CTC TAC TAC ACC TGC CCT CAG CAT TTC ACC | | | | | | | | | | 987 |
| Ala Ile Asp Asp Pro Leu Leu Tyr Tyr Thr Cys Pro Gln His Phe Thr | | | | | | | | | | |
|         190             195             200 | | | | | | | | | | |
| GCG TAC TGC GGC TTC GAC GTA CTC GCG CAC GGC AGT GAG CCT TTC GTT | | | | | | | | | | 1035 |
| Ala Tyr Cys Gly Phe Asp Val Leu Ala His Gly Ser Glu Pro Phe Val | | | | | | | | | | |
|         205             210             215 | | | | | | | | | | |
| TCT CGT CTC GAT TTC GCG CCT TCG CTC GGT AAC GCG ATC TAC TCG GTC | | | | | | | | | | 1083 |
| Ser Arg Leu Asp Phe Ala Pro Ser Leu Gly Asn Ala Ile Tyr Ser Val | | | | | | | | | | |
| 220             225             230 | | | | | | | | | | |
| GAG TTG GTC GCG AAG AAC CTG CGC GAG GCC GTC TTC GAG CCG CGT AAC | | | | | | | | | | 1131 |
| Glu Leu Val Ala Lys Asn Leu Arg Glu Ala Val Phe Glu Pro Arg Asn | | | | | | | | | | |
| 235             240             245             250 | | | | | | | | | | |

| | | | | | | | | | | | | | | | | |
|---|---|---|---|---|---|---|---|---|---|---|---|---|---|---|---|---|
|CTC|AAG|GCG|CGC|GAG|GGA|ATG|ATG|AAC|GCG|CAG|TAC|ATT|GCC|GGA|CAG|1179|
|Leu|Lys|Ala|Arg|Glu|Gly|Met|Met|Asn|Ala|Gln|Tyr|Ile|Ala|Gly|Gln| |
| | | | |255| | | |260| | | | |265| | | |
|GCC|TTC|AAC|TCC|GGT|GGC|CTC|GGC|ATC|GTT|CAC|TCG|ATC|TCG|CAC|GCG|1227|
|Ala|Phe|Asn|Ser|Gly|Gly|Leu|Gly|Ile|Val|His|Ser|Ile|Ser|His|Ala| |
| | | |270| | | | |275| | | | |280| | | |
|GTC|AGT|GCA|TTC|TTC|GAC|AGC|CAC|CAC|GGT|TTG|AAC|AAC|GCC|ATC|GCG|1275|
|Val|Ser|Ala|Phe|Phe|Asp|Ser|His|His|Gly|Leu|Asn|Asn|Ala|Ile|Ala| |
| | |285| | | | |290| | | | |295| | | | |
|TTG|CCG|CGT|GTG|TGG|GAG|TAC|AAC|CTG|CCT|TCG|CGT|TAC|GAG|CGC|TAC|1323|
|Leu|Pro|Arg|Val|Trp|Glu|Tyr|Asn|Leu|Pro|Ser|Arg|Tyr|Glu|Arg|Tyr| |
| |300| | | | |305| | | | |310| | | | | |
|GCC|CAG|TTG|GCC|GGC|GCA|CTC|GGT|GTC|GAC|ACT|CGC|AAC|CTC|ACC|ACG|1371|
|Ala|Gln|Leu|Ala|Gly|Ala|Leu|Gly|Val|Asp|Thr|Arg|Asn|Leu|Thr|Thr| |
|315| | | | |320| | | | |325| | | | |330| |
|GTT|CAG|GCC|GCG|GAT|GCT|GCC|GTC|GAG|GCT|GCC|ATT|CGT|CTG|GCC|AAG|1419|
|Val|Gln|Ala|Ala|Asp|Ala|Ala|Val|Glu|Ala|Ala|Ile|Arg|Leu|Ala|Lys| |
| | | | |335| | | | |340| | | | |345| | |
|GAC|GTC|GGT|ATC|CCC|GAC|AAC|TTC|GGG|CAG|GTT|CGC|ACA|GAC|TCG|TAC|1467|
|Asp|Val|Gly|Ile|Pro|Asp|Asn|Phe|Gly|Gln|Val|Arg|Thr|Asp|Ser|Tyr| |
| | | |350| | | | |355| | | | |360| | | |
|GCG|AAG|AAC|CAG|ATG|AAC|ACC|AAG|AAG|TAC|GAG|GGT|CGT|GGT|GAT|GTC|1515|
|Ala|Lys|Asn|Gln|Met|Asn|Thr|Lys|Lys|Tyr|Glu|Gly|Arg|Gly|Asp|Val| |
| | |365| | | | |370| | | | |375| | | | |
|ATC|AAG|GGT|GAC|GAG|AAG|ACT|GTG|CGC|GCC|ATC|TCC|GAG|CAC|ATT|CAG|1563|
|Ile|Lys|Gly|Asp|Glu|Lys|Thr|Val|Arg|Ala|Ile|Ser|Glu|His|Ile|Gln| |
| |380| | | | |385| | | | |390| | | | | |
|GAC|GAC|TGG|TGC|ACC|CCG|GGT|AAC|CCC|CGT|GAG|GTC|ACT|GTG|GAG|TCG|1611|
|Asp|Asp|Trp|Cys|Thr|Pro|Gly|Asn|Pro|Arg|Glu|Val|Thr|Val|Glu|Ser| |
|395| | | | |400| | | | |405| | | | |410| |
|ATG|ATC|CCG|GTT|GTC|GAT|CAC|GCG|ATC|AAC|AAG|TCG|TAC|TT| | |1652|
|Met|Ile|Pro|Val|Val|Asp|His|Ala|Ile|Asn|Lys|Ser|Tyr| | | | |
| | | | |415| | | | |420| | | | | | | |
|CTAGCAGGGC|CTCCGGCCCC|GTGCGCGCTT|AAGGAGTCCA|GAGACTCCTC|GAGCGCGCAC| | | | | | | | | | |1712|
|AGGGGCTGTG|CCCCTATCGA|AAGGTATTCC|ATG|TCC|GGT|CGC|AGT|TTC|TCC|AGC| | | | | |1766|
| | | |Met|Ser|Gly|Arg|Ser|Phe|Ser|Ser| | | | | | |
| | | |1| | | | |5| | | | | | | | |
|GGA|ATC|GAA|GTG|AAA|GAT|GCT|CTG|CGA|GAG|CAG|GAC|TAC|ATT|GCC|GAT|1814|
|Gly|Ile|Glu|Val|Lys|Asp|Ala|Leu|Arg|Glu|Gln|Asp|Tyr|Ile|Ala|Asp| |
| | |10| | | | |15| | | | |20| | | | |
|GAC|GAG|TTC|GCG|GTA|GTC|GTT|CAT|CTG|GCG|ACG|GCG|CTG|GGG|CGT|CCG|1862|
|Asp|Glu|Phe|Ala|Val|Val|Val|His|Leu|Ala|Thr|Ala|Leu|Gly|Arg|Pro| |
|25| | | | |30| | | | |35| | | | |40| |
|CTC|CTG|CTC|GAA|GGG|CCG|GCC|GGT|GTC|GGT|AAG|ACG|GAA|CTG|GCG|AAG|1910|
|Leu|Leu|Leu|Glu|Gly|Pro|Ala|Gly|Val|Gly|Lys|Thr|Glu|Leu|Ala|Lys| |
| | | | |45| | | | |50| | | | |55| | |
|TCT|CTG|GCT|GCG|ATC|GGG|GGC|CGC|AAA|CTG|GTG|CGA|TTG|CAG|TGT|TAC|1958|
|Ser|Leu|Ala|Ala|Ile|Gly|Gly|Arg|Lys|Leu|Val|Arg|Leu|Gln|Cys|Tyr| |
| | | |60| | | | |65| | | | |70| | | |
|GAA|GGG|CTG|GAC|GAC|AAT|CGA|GCC|CTG|TAC|GAA|TGG|GAC|TAC|GCG|AAC|2006|
|Glu|Gly|Leu|Asp|Asp|Asn|Arg|Ala|Leu|Tyr|Glu|Trp|Asp|Tyr|Ala|Asn| |
| | |75| | | | |80| | | | |85| | | | |
|GAA|CTC|CTG|CAC|GTG|CAG|ATG|CTT|CGC|GAC|CGG|ATC|AGT|GAT|CAG|GTT|2054|
|Glu|Leu|Leu|His|Val|Gln|Met|Leu|Arg|Asp|Arg|Ile|Ser|Asp|Gln|Val| |
| |90| | | | |95| | | | |100| | | | | |
|TCC|GAA|TT|C| | | | | | | | | | | | |2063|
|Ser|Glu| | | | | | | | | | | | | | | |
|105| | | | | | | | | | | | | | | | |

( 2 ) INFORMATION FOR SEQ ID NO:2:

( i ) SEQUENCE CHARACTERISTICS:
        ( A ) LENGTH: 423 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Ile  Glu  Leu  Asn  Gln  Ile  Trp  Asp  Phe  Pro  Ile  Lys  Glu  Phe
 1              5                        10                       15
His  Pro  Phe  Pro  Arg  Ala  Leu  Met  Gly  Val  Gly  Ala  His  Asp  Ile  Ile
               20                        25                       30
Gly  Val  Glu  Ala  Lys  Asn  Leu  Gly  Phe  Lys  Arg  Thr  Leu  Leu  Met  Thr
               35                        40                       45
Thr  Gly  Leu  Arg  Gly  Ser  Gly  Ile  Ile  Glu  Glu  Leu  Val  Gly  Lys  Ile
       50                        55                       60
Glu  Tyr  Gln  Gly  Val  Glu  Val  Val  Leu  Tyr  Asp  Lys  Val  Glu  Ser  Asn
 65                        70                       75                       80
Pro  Lys  Asp  Tyr  Asn  Val  Met  Glu  Ala  Ala  Ala  Leu  Tyr  Gln  Lys  Glu
                         85                       90                       95
Lys  Cys  Asp  Ser  Ile  Ile  Ser  Ile  Gly  Gly  Gly  Ser  Ser  His  Asp  Ala
                    100                      105                      110
Ala  Lys  Gly  Ala  Arg  Val  Val  Ile  Ala  His  Asp  Gly  Arg  Asn  Ile  Asn
                    115                      120                      125
Glu  Phe  Glu  Gly  Phe  Ala  Lys  Ser  Thr  Asn  Lys  Glu  Asn  Pro  Pro  His
          130                      135                      140
Ile  Ala  Val  Ser  Thr  Thr  Ala  Gly  Thr  Gly  Ser  Glu  Thr  Ser  Trp  Ala
 145                     150                      155                      160
Tyr  Val  Ile  Thr  Asp  Thr  Ser  Asp  Met  Asn  Asn  Pro  His  Lys  Trp  Val
                    165                      170                      175
Gly  Phe  Asp  Glu  Ala  Thr  Ile  Val  Thr  Leu  Ala  Ile  Asp  Asp  Pro  Leu
                    180                      185                      190
Leu  Tyr  Tyr  Thr  Cys  Pro  Gln  His  Phe  Thr  Ala  Tyr  Cys  Gly  Phe  Asp
          195                      200                      205
Val  Leu  Ala  His  Gly  Ser  Glu  Pro  Phe  Val  Ser  Arg  Leu  Asp  Phe  Ala
 210                     215                      220
Pro  Ser  Leu  Gly  Asn  Ala  Ile  Tyr  Ser  Val  Glu  Leu  Val  Ala  Lys  Asn
 225                     230                      235                      240
Leu  Arg  Glu  Ala  Val  Phe  Glu  Pro  Arg  Asn  Leu  Lys  Ala  Arg  Glu  Gly
                    245                      250                      255
Met  Met  Asn  Ala  Gln  Tyr  Ile  Ala  Gly  Gln  Ala  Phe  Asn  Ser  Gly  Gly
                    260                      265                      270
Leu  Gly  Ile  Val  His  Ser  Ile  Ser  His  Ala  Val  Ser  Ala  Phe  Phe  Asp
          275                      280                      285
Ser  His  His  Gly  Leu  Asn  Asn  Ala  Ile  Ala  Leu  Pro  Arg  Val  Trp  Glu
 290                     295                      300
Tyr  Asn  Leu  Pro  Ser  Arg  Tyr  Glu  Arg  Tyr  Ala  Gln  Leu  Ala  Gly  Ala
 305                     310                      315                      320
Leu  Gly  Val  Asp  Thr  Arg  Asn  Leu  Thr  Thr  Val  Gln  Ala  Ala  Asp  Ala
                    325                      330                      335
Ala  Val  Glu  Ala  Ala  Ile  Arg  Leu  Ala  Lys  Asp  Val  Gly  Ile  Pro  Asp
                    340                      345                      350
Asn  Phe  Gly  Gln  Val  Arg  Thr  Asp  Ser  Tyr  Ala  Lys  Asn  Gln  Met  Asn
          355                      360                      365
```

-continued

```
Thr  Lys  Lys  Tyr  Glu  Gly  Arg  Gly  Asp  Val  Ile  Lys  Gly  Asp  Glu  Lys
     370                 375                      380

Thr  Val  Arg  Ala  Ile  Ser  Glu  His  Ile  Gln  Asp  Asp  Trp  Cys  Thr  Pro
385                      390                     395                      400

Gly  Asn  Pro  Arg  Glu  Val  Thr  Val  Glu  Ser  Met  Ile  Pro  Val  Val  Asp
                    405                      410                     415

His  Ala  Ile  Asn  Lys  Ser  Tyr
                    420
```

( 2 ) INFORMATION FOR SEQ ID NO:3:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Ser  Gly  Arg  Ser  Phe  Ser  Ser  Gly  Ile  Glu  Val  Lys  Asp  Ala  Leu
1                   5                        10                      15

Arg  Glu  Gln  Asp  Tyr  Ile  Ala  Asp  Asp  Glu  Phe  Ala  Val  Val  Val  His
                    20                       25                      30

Leu  Ala  Thr  Ala  Leu  Gly  Arg  Pro  Leu  Leu  Leu  Glu  Gly  Pro  Ala  Gly
               35                   40                        45

Val  Gly  Lys  Thr  Glu  Leu  Ala  Lys  Ser  Leu  Ala  Ala  Ile  Gly  Gly  Arg
     50                        55                        60

Lys  Leu  Val  Arg  Leu  Gln  Cys  Tyr  Glu  Gly  Leu  Asp  Asp  Asn  Arg  Ala
65                       70                        75                      80

Leu  Tyr  Glu  Trp  Asp  Tyr  Ala  Asn  Glu  Leu  Leu  His  Val  Gln  Met  Leu
                    85                        90                      95

Arg  Asp  Arg  Ile  Ser  Asp  Gln  Val  Ser  Glu
                    100                      105
```

( 2 ) INFORMATION FOR SEQ ID NO:4:

( i ) SEQUENCE CHARACTERISTICS:
        ( A ) LENGTH: 46 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
Ala  Ile  Glu  Leu  Asn  Gln  Ile  Trp  Asp  Phe  Pro  Ile  Lys  Glu  Phe  His
1                   5                        10                      15

Pro  Phe  Pro  Arg  Ala  Leu  Met  Gly  Val  Gly  Ala  His  Asp  Ile  Ile  Gly
                    20                       25                      30

Val  Glu  Ala  Lys  Asn  Leu  Gly  Phe  Lys  Arg  Thr  Leu  Leu  Met
               35                   40                        45
```

DSZD UTILIZATION IN DESULFURIZATION OF DBT BY RHODOCOCCUS SP. IGTS8

RELATED APPLICATIONS

This application claims priority to U.S. Provisional Application Ser. No. 60/004,105 filed Sep. 21, 1995, the contents of which is incorporated herein by reference in its entirety.

BACKGROUND OF THE INVENTION

The microbial desulfurization of fossil fuels has been an area of active investigation for over fifty years. The object of these investigations has been to develop biotechnology based methods for the pre-combustion removal of sulfur from fossil fuels, such as coal, crude oil and petroleum distillates. The driving forces for the development of desulfurization methods are the increasing levels of sulfur in fossil fuel and the increasingly stringent regulation of sulfur emissions. Monticello et al., "Practical Considerations in Biodesulfurization of Petroleum," IGT's 3d Intl. Symp. on Gas, Oil, Coal and Env. Biotech., (Dec. 3–5, 1990) New Orleans, La.

Many biocatalysts and processes have been developed to desulfurize fossil fuels, including those described in U.S. Pat. Nos. 5,356,801, 5,358,870, 5,358,813, 5,198,341, 5,132,219, 5,344,778, 5,104,801 and 5,002,888, incorporated herein by reference. Economic analyses indicate that one limitation in the commercialization of the technology is improving the reaction rates and specific activities of the biocatalysts, such as the bacteria and enzymes that are involved in the desulfurization reactions. The reaction rates and specific activities (sulfur removed/hour/gram of biocatalyst) that have been reported in the literature are much lower than those necessary for optimal commercial technology. Therefore, improvements in the longevity and specific activity of the biocatalyst are desirable.

SUMMARY OF THE INVENTION

The invention relates to the discovery that a class of proteins, one of which was recently purified from Rhodococcus sp. IGTS8, activates two monooxygenases (DszC and DszA) involved in the desulfurization of fossil fuels. Neither DszC nor A are enzymatically active when purified to homogeneity; however, upon the addition of this additional protein (designated DszD herein), enzymatic activity is restored. The function of this protein is believed to couple the oxidation of NADH with the oxygenation of the substrate molecule. A search of the sequence databases revealed that DszD is equivalent to another recently identified Rhodococcus protein, ThcE, which is induced by growth in the presence of atrazine, thiocarbamate herbicides and primary alcohols. Based upon sequence similarity, ThcE appears to be a member of the group III alcohol dehydrogenases, or oxidoreductases, designated alcohol: N,N'-dimethyl-3-nitrosoaniline oxidoreductases. DszD has a monomer molecular weight of approximately 50,000 (by SDS-PAGE) but behaves as a multimeric protein (decamer) on HPLC size exclusion chromatography. The activation of DszC and A by DszD follows saturation kinetics.

Thus, the invention relates to the discovery that the rate of microbial desulfurization of fossil fuels is enhanced or activated by or dependent upon the addition of an oxidoreductase to the biocatalyst or reaction medium. The invention is drawn to a method for enhancing the rate of desulfurizing a fossil fuel containing organic sulfur compounds, comprising the steps of:

a) contacting the fossil fuel with an aqueous phase containing a biocatalyst or biocatalysts capable of cleaving carbon-sulfur bonds (such as Dsz A, Dsz B and/or Dsz C) and a rate-enhancing amount of an oxidoreductase, thereby forming a fossil fuel and aqueous phase mixture;

b) maintaining the mixture of step (a) under conditions sufficient for cleavage of the carbon-sulfur bonds of the organic sulfur molecules by the biocatalyst, thereby resulting in a fossil fuel having a reduced organic sulfur content; and c) separating the fossil fuel having a reduced organic sulfur content from the resulting aqueous phase.

The invention also relates to enhancing the rate of the reaction catalyzed by DszA and/or DszC with a rate enhancing amount of oxidoreductase. This can be accomplished, for example, by adding the oxidoreductase to a biocatalyst or by causing expression or overexpression of the oxidoreductase in a biocatalyst.

In yet another embodiment, the invention relates to a recombinant microorganism containing one or more recombinant DNA molecules which encode a biocatalyst capable of catalyzing one or more steps in a process for desulfurizing a fossil fuel containing organic sulfur molecules and which encode an oxidoreductase.

The invention includes a composition comprising (a) a biocatalyst capable of catalyzing one or more steps in a process for desulfurizing a fossil fuel containing organic sulfur molecules and (b) an oxidoreductase.

BRIEF DESCRIPTION OF THE DRAWINGS

FIG. 6 sets forth the DNA sequence and putative amino acid sequence of the ThcE (DszD) gene.

DETAILED DESCRIPTION OF THE INVENTION

Figure 1:
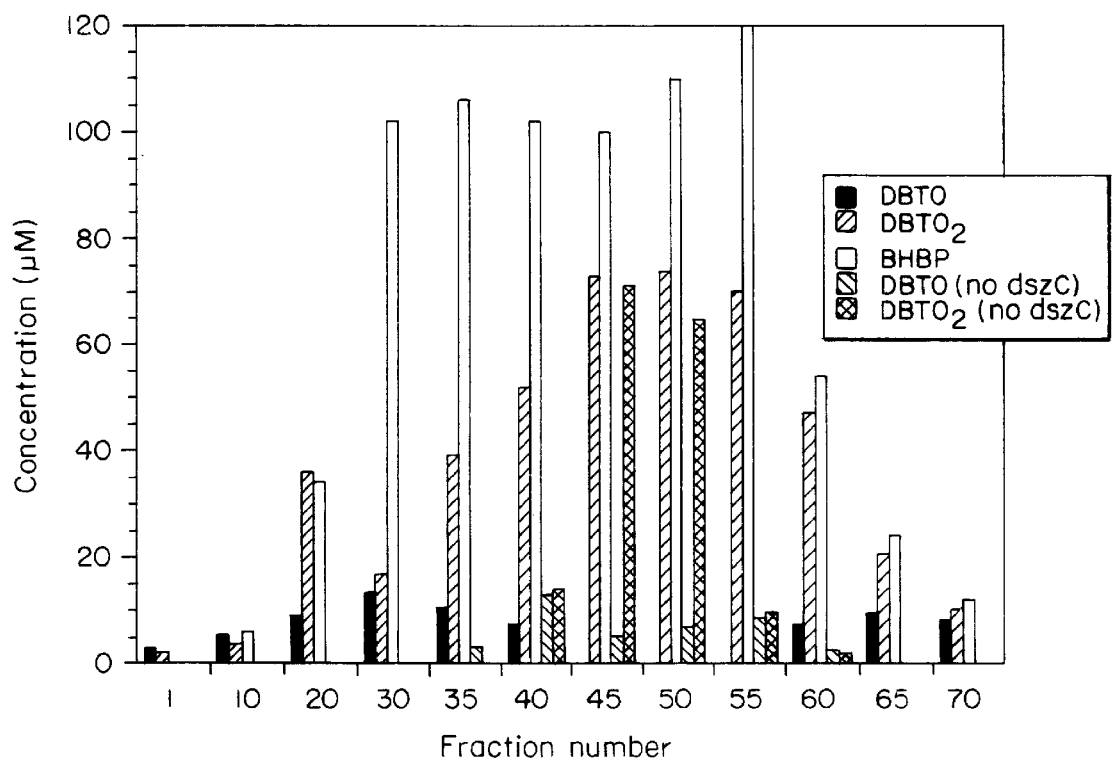
FIG. 1 is a graphic illustration of DszC and A activity after ion exchange chromatography. DszC (15 µg) was added to each fraction and tested for conversion from DBT to DBTO and DBTO2. DszA (5 µg) was added to each fraction and tested for DBT sultone to BHBP conversion. Endogenous DszC activity was also tested.

In the petroleum extraction and refining arts, the term "organic sulfur" is generally understood as referring to organic molecules having a hydrocarbon framework to which one or more sulfur atoms (called heteroatoms) are covalently joined. These sulfur atoms can be joined directly to the hydrocarbon framework, e.g., by one or more carbon-sulfur bonds, or can be present in a substituent joined to the hydrocarbon framework of the molecule, e.g., a sulfate group. The general class of organic molecules having one or more sulfur heteroatoms are referred to as "organosulfur compounds". The hydrocarbon portion of these compounds can be aliphatic, aromatic, or partially aliphatic and partially aromatic.

Cyclic or condensed multicyclic organosulfur compounds in which one or more sulfur heteroatoms are linked directly or indirectly to adjacent carbon atoms in the hydrocarbon framework by aromatic carbon-sulfur bonds are referred to as "sulfur-bearing heterocycles". The sulfur that is present in many types of sulfur-bearing heterocycles is referred to as "thiophenic sulfur" in view of the five-membered aromatic ring in which the sulfur heteroatom is present. The simplest such sulfur-bearing heterocycle is thiophene, which has the composition $C_4H_4S$.

Sulfur-bearing heterocycles are known to be stable to conventional desulfurization treatments, such as hydrodesulfurization (HDS). Sulfur-bearing heterocycles can have relatively simple or relatively complex chemical structures. In complex heterocycles, multiple condensed aromatic rings, one or more of which can be heterocyclic, are present. The difficulty of desulfurization increases with the structural complexity of the molecule. That is, refractory behavior is most accentuated in complex sulfur-bearing heterocycles, such as dibenzothiophene (DBT, $C_{12}H_8S$).

DBT is a sulfur-bearing heterocycle that has a condensed, multiple aromatic ring structure in which a five-membered thiophenic ring is flanked by two six-membered benzylic rings. Much of the residual post-HDS organic sulfur in fossil fuel refining intermediates and combustible products is thiophenic sulfur. The majority of this residual thiophenic sulfur is present as DBT and derivatives thereof having one or more alkyl or aryl groups attached to one or more carbon atoms present in one or both flanking benzylic rings. DBT itself is accepted in the relevant arts as a model compound illustrative of the behavior of the class of compounds encompassing DBT and derivatives thereof in reactions involving thiophenic sulfur. Monticello and Finnerty, *Annual Reviews in Microbiology* 39:371–389. (1985) at 372–373. DBT and derivatives thereof can account for a significant percentage of the total sulfur content of particular crude oils, coals and bitumen. For example, these sulfur-bearing heterocycles have been reported to account for as much as 70 wt % of the total sulfur content of West Texas crude oil, and up to 40 wt % of the total sulfur content of some Middle East crude oils. Thus, DBT is considered to be particularly relevant as a model compound for the forms of thiophenic sulfur found in fossil fuels, such as crude oils, coals or bitumen of particular geographic origin, and various refining intermediates and fuel products manufactured therefrom. Id. Another characteristic of DBT and derivatives thereof is that, following a release of fossil fuel into the environment, these sulfur-bearing heterocycles persist for long periods of time without significant biodegradation. Gundlach et al. *Science* 221:122–129 (1983). It is, therefore, desirable to remove these organosulfur compounds from fossil fuels or other carbonaceous materials which contain them.

A fossil fuel or carbonaceous material that is suitable for desulfurization treatment according to the present invention is one that contains organic sulfur. Such a fossil fuel is referred to as a "substrate fossil fuel". Substrate fossil fuels that are rich in thiophenic sulfur are particularly suitable for desulfurization according to the method described herein. Examples of such substrate fossil fuels include Cerro Negro or Orinoco heavy crude oils; Athabascan tar and other types of bitumen; petroleum refining fractions such as light cycle oil, heavy atmospheric gas oil, and No. 1 diesel oil; and coal-derived liquids manufactured from sources such as Pocahontas #3, Lewis-Stock, Australian Glencoe or Wyodak coal.

Biocatalytic desulfurization, or BDS, is the excision, liberation or removal of sulfur from organosulfur compounds, including refractory organosulfur compounds such as sulfur-bearing heterocycles, as a result of the oxidative cleavage (preferably selectively) of carbon-sulfur bonds in said compounds by a biocatalyst. BDS treatment yields the desulfurized hydrocarbon framework of the former refractory organosulfur compound, along with inorganic sulfur substances which can be readily separated from each other by known techniques such as fractional distillation or water extraction. For example, DBT is "converted" into hydroxybiphenyl when subjected to BDS treatment.

BDS is carried out by biocatalyst(s). Biocatalysts include one or more non-human organisms (e.g., recombinant and non-recombinant, viable and non-viable microorganisms) that functionally express one or more enzymes that direct, singly or in concert with each other, the removal of sulfur from organosulfur compounds, including sulfur-bearing heterocycles, by the oxidation of sulfur and/or the cleavage of carbon-sulfur bonds in said compounds; one or more enzymes obtained from such organisms; or a mixture of such organisms and enzymes. Organisms that exhibit one or more biocatalytic activities required for the desulfurization of a fossil fuel or other carbonaceous material are referred to herein as being Dsz+. Organisms that lack such a biocatalytic activity are referred to herein as being Dsz−. A "biocatalyst" is defined herein as a biological material, or a material of biological origin, which possesses the ability to catalyze one or more reactions, in the presence of appropriate co-factors and/or co-enzymes, for example.

The invention relates to the improved removal of sulfur from carbonaceous materials, such as fossil fuels, containing organic sulfur molecules comprising adding a rate-enhancing amount of an oxidoreductase to the biocatalyst capable of desulfurizing the carbonaceous material. The biocatalysts employed herein are, generally, known in the art. Several investigators have reported the genetic modification of naturally-occurring bacteria into mutant strains capable of catabolizing DBT. Kilbane, J. J., *Resour. Cons. Recycl.* 3:69–79 (1990), Isbister, J. D., and R. C. Doyle, U.S. Pat. No. 4,562,156 (1985), and Hartdegan, F. J. et al., *Chem. Eng. Progress* 63–67 (1984). Many of these mutants desulfurize DBT nonspecifically. Thus, a portion of the fuel value is lost through this microbial action. Isbister and Doyle reported the derivation of a mutant strain of Pseudomonas which appeared to be capable of selectively liberating sulfur from DBT.

Kilbane has reported the mutagenesis of a mixed bacterial culture, thereby producing a bacterium which is capable of selectively liberating sulfur from DBT by an oxidative pathway. This culture was composed of bacteria which can be obtained from natural sources, such as sewage sludge, petroleum refinery wastewater, garden soil, coal, tar-contaminated soil, etc., and maintained in culture under conditions of continuous sulfur deprivation in the presence of DBT. The culture was then exposed to the chemical mutagen 1-methyl-3-nitro-1-nitrosoguanidine. The major catabolic product of DBT metabolism by this mutant culture was hydroxybiphenyl; sulfur was released as inorganic water-soluble sulfate, and the hydrocarbon portion of the molecule remained essentially intact as monohydroxybiphenyl. Kilbane, J. J., *Resour. Cons. Recycl.* 3:69–79 (1990), the teachings of which are incorporated herein by reference.

Kilbane has also isolated a mutant strain of Rhodococcus from this mixed bacterial culture. This mutant, IGTS8 or ATCC No. 53968, is a particularly preferred biocatalyst for use with the instant invention. The isolation and characteristics of this mutant are described in detail in J. J. Kilbane, U.S. Pat. No. 5,104,801, the teachings of which are incorporated herein by reference. This microorganism has been deposited at the American Type Culture Collection (ATCC), 12301 Park Lawn Drive, Rockville, Md., U.S.A. 20852 under the terms of the Budapest Treaty, and has been designated as ATCC Deposit No. 53968. One suitable ATCC No. 53968 biocatalyst preparation is a culture of the living microorganisms, prepared generally as described in U.S. Pat. No. 5,104,801 and mutants or derivatives thereof (see, e.g. U.S. Pat. No. 5,358,869). Cell-free enzyme preparations obtained from ATCC No. 53968 or mutants thereof generally as described in U.S. Pat. Nos. 5,132,219, 5,344,778 and 5,358,870 can also be used. These enzyme preparations can further be purified and employed.

Other examples of microorganisms that appear to behave in the same or similar manner include the microbial consortium (a mixture of several microorganisms) disclosed in Kilbane (1990), 3 Resour. Conserv. Recycl. 69–79, the microorganisms disclosed by Kilbane in U.S. Pat. Nos. 5,002,888 (issued Mar. 26, 1991), 5,104,801 (issued Apr. 14, 1992), 5,344,778, 5,132,219, 5,198,341, 5,344,778, 5,356, 813, 5,356,801, 5,358,869, 5,358,870 [also described in Kilbane (1990), *Biodesulfurization: Future Prospects in Coal Cleaning,* in Proc, 7th Ann. Int'l. Pittsburgh Coal Conf. 373–382], and 5,198,341 (issued Mar. 30, 1993); and by Omori et al. (1992), *Desulfurization of dibenzothiophene by Corynebacterium sp. strain SY*1, 58 Appl. Env. Microbiol. (No. 3) 911–915; and Izumi et al., *Applied and Environmental Microbiology* 60:223–226 (1994) all incorporated herein by reference.

Each of the foregoing microorganisms can function as a biocatalyst in the present invention because each produces one or more enzymes (protein biocatalysts) that carry out the specific chemical reaction(s) by which sulfur is excised from refractory organosulfur compounds. Mutational or genetically engineered derivatives of any of the foregoing microorganisms, as exemplified by the U.S. patents listed above, can also be used as the biocatalyst herein, provided that appropriate biocatalytic function is retained.

Additional microorganisms suitable for use as the biocatalyst or biocatalyst source in the desulfurization process now described can be derived from naturally occurring microorganisms by known techniques. As set forth above, these methods include culturing preparations of microorganisms obtained from natural sources such as sewage sludge, petroleum refinery wastewater, garden soil, or coal, tar-contaminated soil under selective culture conditions in which the microorganisms are grown in the presence of refractory organosulfur compounds such as sulfur-bearing heterocycles as the sole sulfur source; exposing the microbial preparation to chemical or physical mutagens; or a combination of these methods. Such techniques are recounted by Isbister and Doyle in U.S. Pat. No. 4,562,156 (issued Dec. 31, 1985); by Kilbane in 3 Resour. Conserv. Recycl. 69–79 (1990), U.S. Pat. Nos. 5,002,888, 5,104,801 and 5,198,341; and by Omori and coworkers in 58 Appl. Env. Microbiol. (No. 3) 911–915 (1992), all incorporated by reference.

As explained above, enzymes are protein or peptide biocatalysts which can be made by living cells. Enzymes promote, direct or facilitate the occurrence of a specific chemical reaction or series of reactions (referred to as a pathway), generally, without themselves becoming consumed as a result thereof. Enzymes can include one or more unmodified or post-translationally or synthetically modified polypeptide chains or fragments or portions thereof, which catalyze the desired reaction or series of reactions when in the presence of the appropriate additional coenzymes, cofactors, or coreactants. The reaction or series of reactions relevant to one embodiment of the present invention culminates in the excision of sulfur from the hydrocarbon framework of a refractory organosulfur compound, such as a sulfur-bearing heterocycle. The hydrocarbon framework of the former refractory organosulfur compound remains substantially intact. Microorganisms or enzymes employed as biocatalysts in the present invention preferably and advantageously do not consume the hydrocarbon framework of the former refractory organosulfur compound as a carbon source for growth. As a result, the fuel value of substrate fossil fuels exposed to BDS treatment does not deteriorate.

Although living microorganisms (e.g., a culture) can be used as the biocatalyst herein, this is not required. Biocatalytic enzyme preparations that are useful in the present invention include microbial lysates, extracts, fractions, subfractions, or purified products obtained by conventional means and capable of carrying out the desired biocatalytic function. Generally, such enzyme preparations are substantially free of intact microbial cells. Kilbane and Monticello disclose enzyme preparations that are suitable for use herein in U.S. Pat. Nos. 5,132,219 (issued Jul. 21, 1992), and 5,358,870 (filed Jun. 11, 1992), for example. Rambosek et al. disclose recombinant microorganisms and enzyme preparations, engineered from Rhodococcus sp. ATCC No. 53968 and suitable for use herein, in U.S. Pat. No. 5,356, 813. In a particularly preferred embodiment, the biocatalyst is overexpressed in the recombinant host cell (such as a cell which contains more than one copy of the gene or genes). For example, The desulfurization of dibenzothiophene by Rhodococcus sp. IGTS8 : has been shown to involve at least three enzymes (designated DszA, B and C), of which DszA and C are now appreciated to be monooxygenases. As such, in a particularly preferred embodiment, the biocatalyst includes one or more of the enzymes, Dsz A, Dsz B and/or Dsz C.

Enzyme biocatalyst preparations suitable for use herein can optionally be affixed to a solid support, e.g., a membrane, filter, polymeric resin, glass particles or beads, or ceramic particles or beads. The use of immobilized enzyme preparations facilitates the separation of the biocatalyst from the reaction medium, such as the treated fossil fuel which has been depleted of refractory organosulfur compounds.

The specific activity of a given biocatalyst is a measure of its biocatalytic activity per unit mass. Thus, the specific activity of a particular biocatalyst depends on the nature or identity of the microorganism used or used as a source of biocatalytic enzymes, as well as the procedures used for preparing and/or storing the biocatalyst preparation. The concentration of a particular biocatalyst can be adjusted as desired for use in particular circumstances. For example, where a culture of living microorganisms (e.g., ATCC No. 53968) is used as the biocatalyst preparation, a suitable culture medium lacking a sulfur source other than sulfur-bearing heterocycles can be inoculated with suitable microorganisms and fermented until a desired culture density is reached. The resulting culture can be diluted with additional medium or another suitable buffer, or microbial cells present in the culture can be retrieved e.g., by centrifugation, and resuspended at a greater concentration than that of the original culture. The concentrations of microorganism and enzyme biocatalyst can be adjusted similarly. In this manner, appropriate volumes of biocatalyst preparations having predetermined specific activities and/or concentrations can be obtained.

As set forth above, a protein (designated DszD) has now been purified from Rhodococcus sp. IGTS8 which activates and enhances the activity of two monooxygenases integral in the biodesulfurization pathway (DszC and DszA). The function of this protein is believed to couple the oxidation of NADH with the oxygenation of the substrate molecules by DszA and DszC.. A search of the sequence databases revealed that DszD is equivalent to another recently isolated Rhodococcus protein, ThcE, which is reported to be induced by growth in the presence of atrazine, thiocarbamate herbicides and primary alcohols. ThcE is a member of the group III alcohol dehydrogenases, or oxidoreductases, designated alcohol: N,N'-dimethyl-3-nitrosoaniline oxidoreductases and has been described in Nagy et al., *Arch. Microbiol* (1995) 163: 439–446, which is incorporated herein by reference in its entirety. DszD has a monomer molecular weight of approximately 50,000 (by SDS-PAGE) but behaves as a multimeric protein (decamer) on HPLC size exclusion chromatography. The activation of DszC and A by DszD follows saturation kinetics.

In view of the above described discovery, desulfurization of DBT can be enhanced by the addition of an oxidoreductase. Suitable oxidoreductases include monooxygenase reductases, or alcohol oxidoreductases, such as N,N'-dimethyl-4-nitrosoaniline (NDMA)-dependent alcohol oxidoreductases (MNO). Group III alcohol dehydrogenases, or oxidoreductases, have been reported to oxidize a primary alcohol and reduce an electron acceptor, such as the nonphysiological compound NDMA. They generally contain a tightly but non-covalently bound molecule of $NAD^+$, which mediates electron transfer between an alcohol and the electron acceptor (e.g., NDMA). The term oxidoreductase is defined herein to include endogenous or wild-type enzymes, recombinantly produced enzymes, fusion proteins, active fragments, mutants or combinations thereof which possess the ability to enhance and/or activate the activity of DszA and/or DszC. Mutants include allelic variants, amino acid or site-directed mutations or derivatives (such as those prepared employing recombinant DNA technology). Alternatively mutants can be made employing other chemical or physical mutagenesis techniques with the host microorganism. The enzyme is preferably isolated from Rhodococcus or of rhodoccocal origin, such as IGTS8 or Rhodococcus sp. N186/21. Other preferred embodiments include recombinant oxidoreductases having an amino acid sequence highly homologous (such as, atleast about 90%) to the amino acid sequence of these enzymes. Alternatively homologous oxidoreductases, such as those which can be isolated from *Amycolatopsis methanolics* and *Mycobacterium gastri* can be employed.

As set forth above, oxidoreductases which can be employed herein include those generally known in the art and can be used directly as found in nature (e.g., a microbial fraction which contains the protein or enzyme), obtained commercially or can be made recombinantly. For example, the DNA and amino acid sequences of DszD is set forth in Nagy et al., *Arch Microbiology* (1995) 163:439–446 (and illustrated in FIG. 6) and can be used to transform a suitable host microorganism as is well known in the art and discussed in U.S. Pat. No. 5,356,801, for example. The DNA sequence can be isolated from a suitable Rhodococcus employing well known techniques, such as PCR.

In another embodiment, the oxidoreductase can be overexpressed by the desulfurization microorganism (such as IGTS8). This can be accomplished, for example, by mutagenesis. Suitable mutagens include radiation, e.g., ultraviolet radiation, and chemical mutagens, such as N-methyl-N'-nitrosoguanidine, hydroxylamine, ethylmethanesulfonate and nitrous acid. The mutagenesis and subsequent screening for mutants harboring increased enzymatic activity can be conducted according to methods generally known in the art.

Where the oxidoreductase is recombinant, the protein can be made and, preferably, overexpressed in situ, such as by the addition of a recombinant microorganism which contains one or more copies of a DNA sequence which encodes the oxidoreductase. In a particularly preferred embodiment, the recombinant microorganism encoding the oxidoreductase also possesses one or more enzymes capable of catalyzing one or more reactions in the biodesulfurization of a fossil fuel, particularly DszA and/or DszC. For example, the DNA encoding oxidoreductase, under control of a suitable promoter, can be transformed into IGTS8 or another microorganism capable of desulfurizing a fossil fuel. In another example, the DNA encoding the oxidoreductase is simultaneously (e.g., presented in a single plasmid or vector) or independently transformed into a common host cell with the DNA encoding the desulfurization biocatalyst(s) or enzymes. The DNA encoding the oxidoreductase can be, for example, under the control of the same or different promoter as the DNA encoding the biocatalyst capable of desulfurizing the fossil fuel. In one embodiment, the oxidoreductase DNA is incorporated or ligated into the desulfurization gene cluster or operon of IGTS8.

The oxidoreductase is added to the reaction mixture in a rate-enhancing amount. "Rate-enhancing amount," as defined herein, is an amount which will significantly increase the rate of reaction of the biocatalyst, as originally obtained, including activating the biocatalyst. For example, where the biocatalyst is IGTS8, a cell-free fraction or purified enzyme preparation thereof, a "rate-enhancing amount" of oxidoreductase is an amount of oxidoreductase that, in addition to that inherently present in the biocatalyst as obtained, will significantly increase the rate of desulfurization. The rate of desulfurization can be increased, for example, by at least 25%, 50% or 100% in comparison to the rate employing the biocatalyst per se. In one embodiment, the oxidoreductase is added to the reaction medium in an amount which achieves or approximates saturation kinetics.

The microorganism harboring the DNA sequence which encodes DszD can be grown under conditions which maximize the expression of the gene. Rhodococcus species which contain the gene can be grown in the presence of an alcohol (such as ethanol, ethanolamine, glycerol or propanol), aldehydes (such as, propionaldehyde), thiocarbamates or atrazine, for example. These compounds may induce or increase the expression of the gene in the microorganism.

As summarized above, the invention described herein relates in one aspect to a DNA molecule or fragment thereof containing a gene or genes which encode an oxidoreductase and/or a biocatalyst capable of desulfurizing a fossil fuel that contains organosulfur compounds. The DNA molecule or fragment thereof can be purified and isolated DNA obtained from, e.g., a natural source, or can be recombinant (heterologous or foreign) DNA that is, e.g., present in a non-human host organism. The DNA can be isolated by well knwon techniques, such as PCR, designing oligonucleotide primers from the nucleotide sequence set forth in FIG. 6.

The recombinant DNA molecules of the present invention include DNA resulting from the insertion into its chain, by chemical or biological means, of one or more genes encoding a biocatalyst capable of selectively cleaving carbon-sulfur bonds and an oxidoreductase, said gene not originally present in that chain. Recombinant DNA includes any DNA synthesized by procedures using restriction nucleases, nucleic acid hybridization, DNA cloning, DNA synthesis or any combination of the preceding. Methods of construction can be found in Maniatis et al., and in other methods known by those skilled in the art.

Procedures for the construction of the DNA plasmids or vectors of the present invention include those described in Maniatis et al. and other methods known by those skilled in the art. The terms "DNA plasmid" and "vector" are intended to encompass any replication competent plasmid or vector capable of having foreign or exogenous DNA inserted into it by chemical or biological means and subsequently, when transformed into an appropriate non-human host organism, of expressing the product of the foreign or exogenous DNA insert (e.g., of expressing the biocatalyst and oxidoreductase of the present invention). In addition, the plasmid or vector must be receptive to the insertion of a DNA molecule or fragment thereof containing the gene or genes of the present invention, said gene or genes encoding a biocatalyst, as defined above. Procedures for the construction of DNA plasmid vectors include those described in Maniatis et al. and others known by those skilled in the art.

The plasmids of the present invention include any DNA fragment containing a gene or genes encoding an oxidoreductase and/or a biocatalyst. The term "plasmid" is intended to encompass any DNA fragment. The DNA fragment should be transmittable, for example, to a host microorganism by transformation or conjugation. Procedures for the construction or extraction of DNA plasmids include those described in Maniatis et al. and others known by those skilled in the art.

The transformed non-human host organisms of the present invention can be created by various methods by those skilled in the art. For example, electroporation as explained by Maniatis et al. can be used. By the term "non-human host organism" is intended any non-human organism capable of the uptake and expression of foreign, exogenous or recombinant DNA. Preferably, the host organism is a bacterium, more preferably a pseudonomad.

In the biocatalytic desulfurization stage, the carbonaceous material or fossil fuel containing sulfur-bearing heterocycles is combined with the biocatalyst and oxidoreducase. The relative amounts of biocatalyst and oxidoreducase and carbonaceous material, such as a fossil fuel, can be adjusted to suit particular conditions, or to produce a particular level of residual sulfur in the treated, desulfurized material. The amount of biocatalyst preparation to be combined with a given quantity of substrate will reflect the nature, concentration and specific activity of the particular biocatalyst(s) and oxidoreductase used, as well as the nature and relative abundance of inorganic and organic sulfur compounds present in the substrate and the degree of desulfurization sought or considered acceptable.

The method of desulfurizing a fossil fuel of the present invention involves two aspects. First, a host organism or biocatalytic preparation obtained therefrom and oxidoreductase is contacted with a fossil fuel to be desulfurized. This can be done in any appropriate container, optionally fitted with an agitation or mixing device. The mixture is combined thoroughly and allowed to incubate for a sufficient time to allow for cleavage of a significant number of carbon-sulfur bonds in organosulfur compounds, thereby producing a desulfurized fossil fuel. In one embodiment, an aqueous emulsion or microemulsion is produced with an aqueous culture of the organism or enzyme fraction and the fossil fuel, allowing the organism to propagate in the emulsion while the expressed biocatalyst cleaves carbon-sulfur bonds.

Variables such as temperature, mixing rate and rate of desulfurization will vary according to the organism biocatalyst and/or oxidoreductase, used. The parameters can be determined through no more than routine experimentation.

Several suitable techniques for monitoring the rate and extent of desulfurization are well-known and readily available to those skilled in the art. Baseline and time course samples can be collected from the incubation mixture, and prepared for a determination of the residual organic sulfur in the fossil fuel. The disappearance of sulfur from organosulfur compounds, such as DBT, in the sample being subjected to biocatalytic treatment can be monitored using, e.g., X-ray fluorescence (XRF) or atomic emission spectrometry (flame spectrometry). Preferably, the molecular components of the sample are first separated, e.g., by gas chromatography.

The process and the biocatalytic compositions (including the recombinant microorganisms) of the claimed invention result in a significant and unexpected improvement over earlier disclosed processes of desulfurization. It has been shown that in vitro the reactions catalyzed by purified DszA and DszC proteins are activated by the addition of the oxidoreductase. This is particularly unexpected in view of recent discussions in the literature suggesting that FAD binds directly to DszC (Denome et al., J. Bacteriol., 176:6707–6716, 1994) and the suggestion that NADH is the only cofactor required for the system (Ohshiro et al., FEMS Microbiol. Lett. 118:341–344, 1994). Others suggest that DszABC are the sole enzymes responsible for desulfurization to occur (Piddington, et al., Appl. Env. Microbiol., 67:468–475, 1995).

Without being limited to any particular mechanism or theory, it is believed that the pathway of the desulfurization reaction is set forth below:

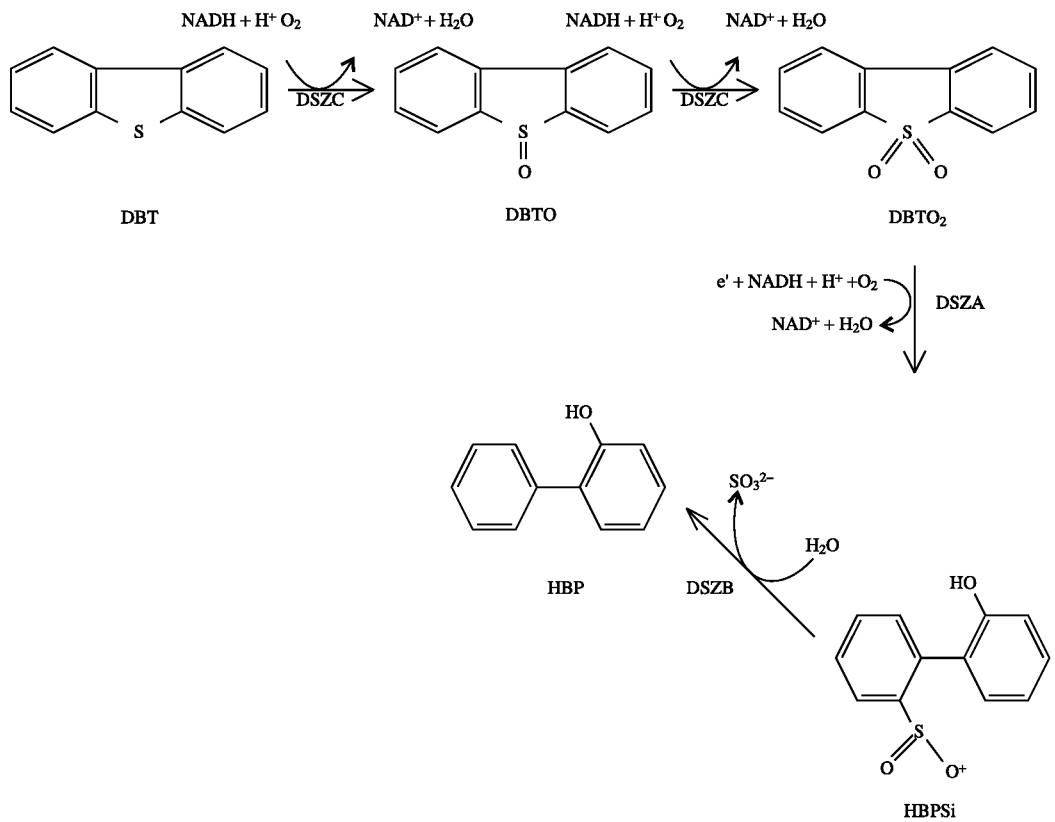

Here, the oxidoreductase is believed to be a short electron transport chain to deliver the reducing equivalents from NADH (or other electron donor) to the enzymes, DszC and/or DszA (possibly a physiological electron acceptor of the oxidoreductase). The enzyme DszC is believed to be responsible for the biocatalysis of the oxidation reaction of DBT to DBTO2. The enzyme DszA is believed to be responsible for the oxygenation of DBTO2 to phenolphenylsulfite (PPS).

It is particularly preferred to add the cofactor, FMN, to the reaction medium as well as an electron donor, NADH or NADPH. Also preferred is the addition of an NADH or NADPH regeneration system for converting NAD+ to NADH, according to methods known in the art.

The invention will now be further illustrated by the way of the following examples.

EXEMPLIFICATION

Growth of Rhodococcus sp. IGTS8:

A sample of frozen stock of Rhodococcus sp. IGTS8 strain CPE-648 containing plasmid pENOK3 (genotype of DszA-B-C+) as described by Piddington et al. (*Appl. Environ. Microbiol.* 61:468–475 (1995)) was grown in 500 ml of rich medium in a 2000 ml shake flask for 48 hours at 30° C. This culture was used to inoculate (4% inoculum) a 15 Liter NBS fermentater in the same medium. This culture was grown for 48 hours at 30° C. while controlling pH (between 6.8 and 7.3), agitation and dissolved oxygen (>50% saturated). Finally a 5% inoculum was transferred to a production-scale fermentater (300 Liter Chemap) containing basal salts medium, 0.5 g/L Ivanhoe antifoam, 8 g/l ethanol and 1.5 mM dimethyl sulfoxide. The culture was grown for 45 hours, achieving an optical density of 11, with a doubling time of 4.3 hours during the first 24 hours of the run. The cell suspension was concentrated through a Westfalia centrifuge resulting in the production of about 2.5 kg. of wet cell paste. The paste was stored at −70° C. until used for purification.

Purification of DszD 150 g (wet cell paste) of the Rhodococcus as grown above were resuspended in 25 mM NaPi, pH 7.5 (buffer A) containing 100 mM NaCl, 0.5 mM DTT, 1' mM PMSF and DNAse. The cell suspension was passed two times through a French pressure cell (at 20,000 psi) and then centrifuged at 30,000×g for 45 minutes (5° C.) to remove unbroken cells and cell debris. All subsequent chromatography steps were performed at 4° C. using a Pharmacia FPLC system. The supernatant was loaded into a Q-sepharose column (2.6 cm ×20 cm) equilibrated with buffer A containing 100 mM NaCl. Following loading the column was washed extensively with the same buffer until the OD280 of the eluent was close to zero. The column was developed with a linear gradient from 100 mM NaCl to 500 mM NaCl in buffer A for 180 minutes at a flow rate of 5 mL/minute and 10 mL fractions were collected. The fractions which displayed DszD activity were pooled and dialyzed overnight vs. buffer A. The dialysate was loaded onto a Toyopearl DEAE-650M column (2.6 cm ×10 cm) equilibrated with buffer A. The column was developed with a linear gradient from 0 to 200 mM NaCl for 90 minutes at a flow rate of 4 mL/minute and 4 mL fractions were collected. The fractions which contained DszD activity were pooled and dialyzed overnight vs. buffer A. The dialysate was loaded onto a Pharmacia MonoQ column equilibrated with buffer A. The column was developed with a linear gradient from 160 to 300 mM NaCl for 30 minutes at a flow rate of 0.5 mL/minute and 0.5 mL fractions were collected. The fractions which displayed DszD activity were pooled and concentrated to 0.2 mL using Amicon microconcentrators (molecular weight cutoff of 10 kDa). The concentrated sample was then applied to a Pharmacia Superdex 75 size exclusion column equilibrated with buffer A containing 100 mM NaCl. The column was eluted with the same buffer at a flow rate of 0.2 mL/minute and 0.2 mL fractions were collected. The fractions containing DszD activity were pooled and concentrated using the microconcentrators and the protein was stored on ice until used. SDS-PAGE analysis (14% polyacrylamide) of the final preparation showed a single band with an approximate monomer molecular weight of 50,000 Da.

Enzyme assays

DszD activity was measured by monitoring DBTO and DBTO2 production from DBT as catalyzed by the combination of DszC and DszD. The DszC was obtained from an *E. coli* expression system, previously described. The assay (in 25 mM NaPi pH 7.5, 100 mM NaCl and 0.5 mM DTT) contained DszC (between 6 and 15 pg), 3 mM NADH, 10 $\mu$M FMN, 100 $\mu$M DBT and the sample containing DszD. The assay mixture was allowed to incubate at 30° C. with shaking at 300 rpm for some period of time (typically 15 to 60 minutes). The reaction was stopped by the addition of acetonitrile (to 50 %) and the products analyzed by reversed phase HPLC. Activation of DszA by DszD was assayed in the same manner (DszA was also obtained from an *E. coli* expression system) except that the substrate was DBT sultone and the product was 2,2'-dihydroxybiphenyl (BHBP).

Results:

Purification of DszD

Figure 2:
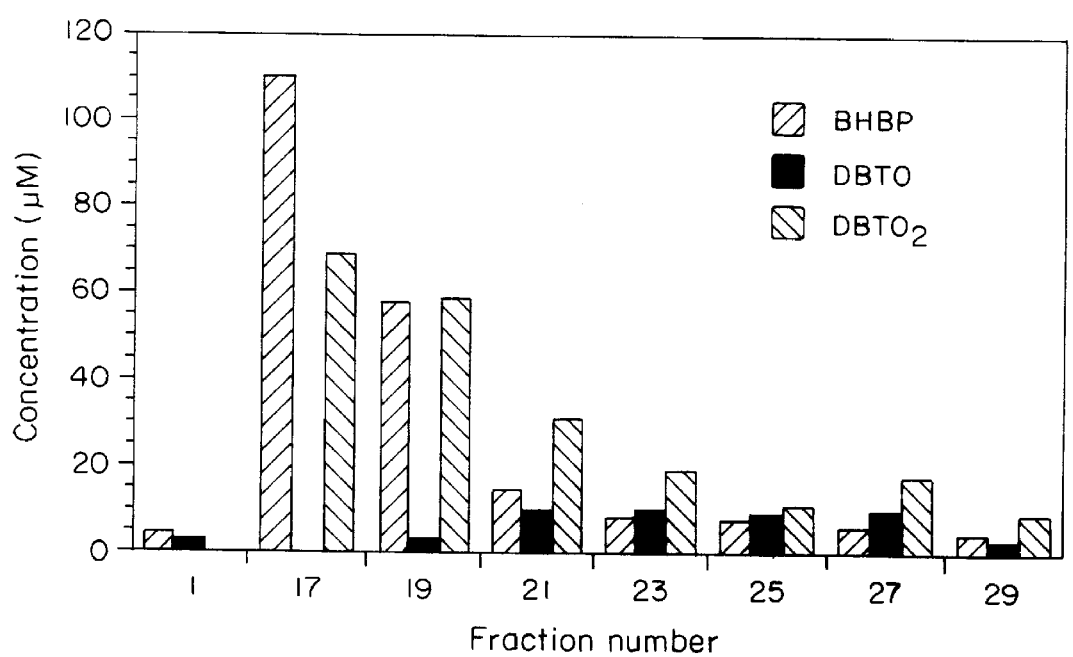
FIG. 2 is a graphic illustration of DszC activity after Superdex 75 size exclusion chromatography. DszC (15 µg) was added to each fraction and tested for conversion from DBT to DBTO2. DszA activity after Superdex 75 size exclusion chromatography. DszA (5 µg) was added to each fraction and tested for DBTsultone to BHBP conversion.
Figure 3:
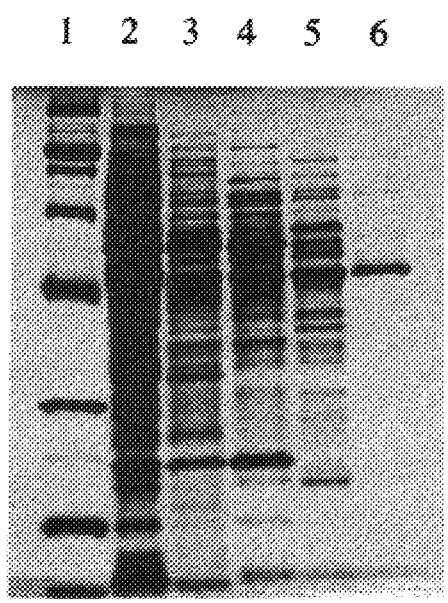
FIG. 3 is an electrophoretic gel illustrating SDS-PAGE (14% acrylamide) of the purification of DszD. Lane 1 presents the molecular weight standards (Biorad, 200, 116, 97.4, 66, 45, 31, 21.5 and 14.5 kDa); lane 2, crude cell lysate; lane 3, after Q-sepharose; lane 4, after Toyopearl-DEAE; lane 5, after MonoQ, and; lane 6, after Superdex 75.

FIG. 1 shows the DszD activity profile of the fractions from the first anion exchange column (Q-sepharose). As can be seen by these data the activity starts around fraction 20 and extends to about fraction 60. Both DszA and C activation occurs in these reactions, furthermore the endogenous DszC activity is also present in these fractions (notably fractions 40 to 50). Fractions 40 to 60 were pooled and further separated on Toyopearl - DEAE. An activity pattern similar to the Q-sepharose column was observed after the Toyopearl - DEAE chromatography except that the activity eluted at a lower salt concentration and endogenous DszC activity occurred in later fractions (a small amount of activity in fraction 40). This was further substantiated by Western analysis which showed that DszC eluted with a peak between fraction 45 and 50 (data not shown). Fractions 15 to 35 were pooled and applied to the MonoQ column. The active fractions from this column were pooled, concentrated and further separated by chromatography over a Superdex 75 FPLC column. The activity profile of this column is shown in FIG. 2. This figure shows that both DszA and C are activated by protein(s) in the same fractions. SDS-PAGE analysis (FIG. 3) showed that the final preparation consisted of a single polypeptide of molecular weight approximately 50,000. HPLC analysis using a TosoHaas TSK3000SW size exclusion column on a Hewlett Packard 1050 HPLC system showed a single protein peak eluted at an approximate mass of 500,000 Da indicating that the native protein is most likely a decamer.

DszD activation of DszC and DszA

Figure 4:
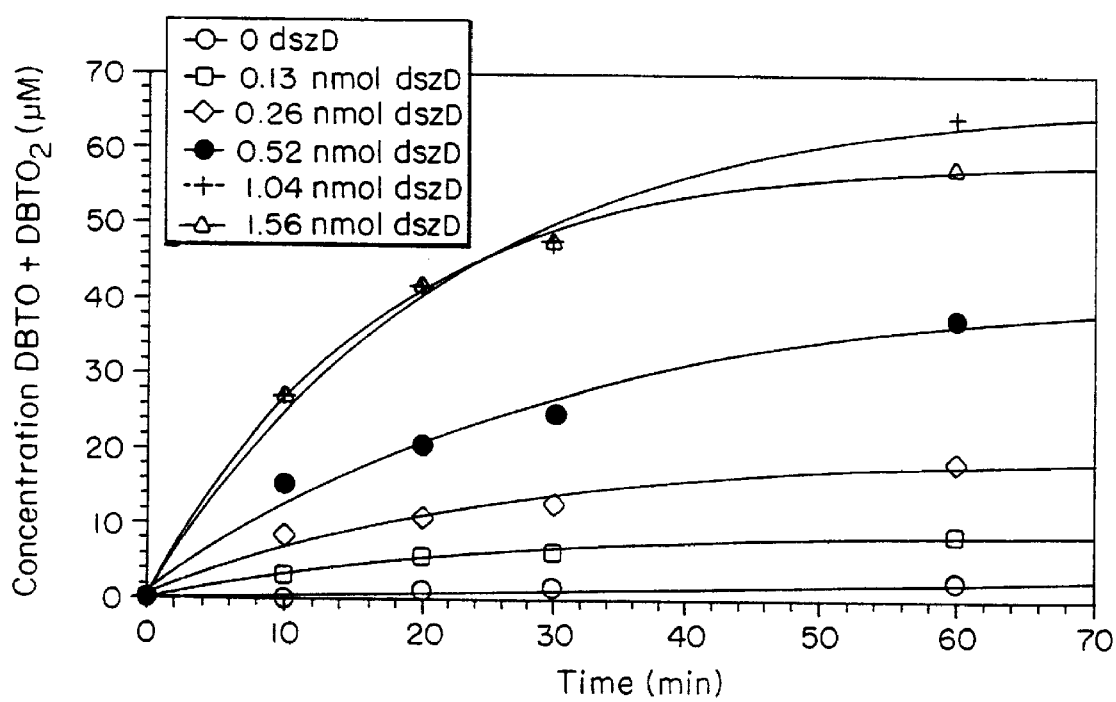
FIG. 4 illustrates the activation of DszC by the addition of increasing amounts of DszD. A fixed amount of DszC (0.33 nmol)) was titrated with increasing amounts of DszD.
Figure 5:
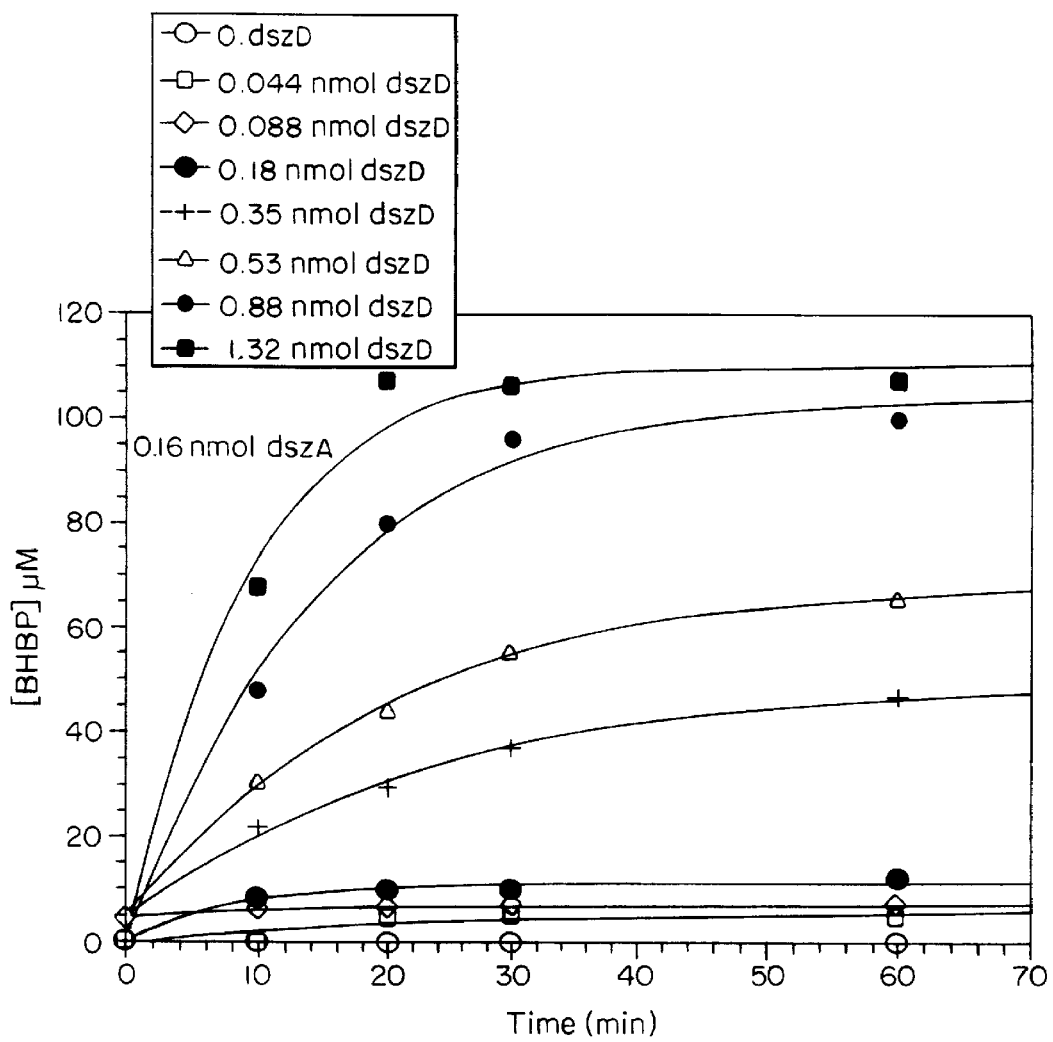
FIG. 5 illustrates activation of DszA by increasing amounts of DszD. A fixed amount of DszA (0.16 nmol) was titrated with increasing amounts of DszD.

FIG. 4 shows that the activation of DszC by DszD follows saturation kinetics. As the ratio between DszD and C is increased an increased rate of DBTO2 formation is observed. A plot of the initial rate vs. DszD:DszC shows that saturation is achieved. FIG. 5 shows the result of activation of DszA by the same preparation. The same effect is observed, i.e. as more DszD is added an increase in the DszA reaction rate occurs.

Amino acid sequence of DszD DszD was subjected to N-terminal sequence and the following sequence was obtained (one letter amino acid abbreviations):

H2N-AIELNQIWDFPIKEFHPFPRALMGVGAHD-IIGVEAKNLGFKRTLLM-COOH (SEQ ID. NO: 4)

A search of the data-bases resulted in a 100% match with a Rhodococcus protein designated ThcE (Nagy et al., *Arch. Microbiol.* 163:439–446 (1995)). The DNA sequence and putative amino acid sequences of the open reading frames are set forth in FIG. 6. This protein has high homology to the alcohol: N,N'-dimethyl-4-nitrosoaniline (NDMA) oxidoreductses found in other Gram-positive organisms which are involved in the oxidation of alcohols and the concomitant reduction of an electron acceptor. The physiological electron acceptor in those organisms is unknown.

EQUIVALENTS

Those skilled in the art will know, or be able to ascertain, using no more than routine experimentation, many equivalents to the specific embodiments of the invention described herein. These and all other equivalents are intended to be encompassed by the following claims.

We claim:

1. An isolated DNA molecule comprising DNA which encodes a group III alcohol dehydrogenase and DNA which encodes a biocatalyst which oxidatively desulfurizes a fossil fuel which contains organic sulfur molecules via nicotinamide adenine dinucleotide-dependent manner.

2. The DNA molecule of claim 1 wherein the group III alcohol dehydrogenase is N,N'-dimethyl-4-nitrosoaniline-dependent alcohol oxidoreductase.

3. The DNA molecule of claim 1 wherein the group III alcohol dehydrogenase is of Rhodococcus origin.

4. The DNA molecule of claim 3 wherein the DNA molecule which encodes the biocatalyst is derived from Rhodococcus sp. ATCC 53968.

5. A microorganism containing a recombinant DNA molecule which encodes:
    (a) a group III alcohol dehydrogenase; and
    (b) one or more biodesulfurization enzymes which are components of a biocatalyst that oxidatively cleaves carbon-sulfur bonds of an organic sulfur molecule in a nicotinamide adenine dinucleotide-dependent manner.

6. The microorganism of claim 5 wherein the group III alcohol dehydrogenase is N,N'-dimethyl-4-nitrosoaniline-dependent alcohol oxidoreductase.

7. The microorganism of claim 5 wherein the DNA which encodes the group III alcohol dehydrogenase is of Rhodococcus origin.

8. The microorganism of claim 7 wherein the DNA which encodes one or more biodesulfurization enzymes is derived from Rhodococcus sp. ATCC 53968.

9. The DNA molecule of claim 3 wherein the group III alcohol dehydrogenase is ThcE.

10. An isolated DNA molecule comprising DNA which encodes a group III alcohol dehydrogenase and DNA which encodes one or more biodesulfurization enzymes selected from the group consisting of DszA, DszB and DszC.

11. The DNA molecule of claim 10 wherein the group III alcohol dehydrogenase is an N,N'-dimethyl-4-nitrosoaniline-dependent alcohol oxidoreductase.

12. The DNA molecule of claim 10 wherein the group III alcohol dehydrogenase is of Rhodococcus origin.

13. The DNA molecule of claim 12 wherein the group III alcohol dehydrogenase is ThcE.

14. The microorganism of claim 5 wherein the biodesulfurization enzymes are selected from the group consisting of DszA, DszB and DszC.

15. The microorganism of claim 14 wherein the group III alcohol dehydrogenase is ThcE.

* * * * *